United States Patent [19]

Inoue et al.

[11] Patent Number: 5,393,899

[45] Date of Patent: Feb. 28, 1995

[54] PROCESS FOR PURIFICATION OF CRUDE 4,4'-DIAMINO-1,1'-DIANTHRAQUINONYL-3,3'-DISULFONIC ACIDS AND SALTS THEREOF

[75] Inventors: Hiroki Inoue, Osaka; Iwao Sakaguchi, Hyogo; Katsutoshi Numano, Osaka; Toshiaki Kishimoto, Osaka; Yoshiaki Hayashi, Osaka; Keisuke Ito, Osaka, all of Japan

[73] Assignee: Sumimoto Chemical Company, Limited, Osaka, Japan

[21] Appl. No.: 108,850

[22] Filed: Aug. 19, 1993

Related U.S. Application Data

[63] Continuation of Ser. No. 818,146, Jan. 8, 1992, abandoned.

[30] Foreign Application Priority Data

Jan. 29, 1991 [JP] Japan .................................. 3-009108
Mar. 15, 1991 [JP] Japan .................................. 3-051129

[51] Int. Cl.$^6$ ............................................. C07D 87/46
[52] U.S. Cl. ..................................... 552/212; 552/211
[58] Field of Search ................................. 552/212, 211

[56] References Cited

U.S. PATENT DOCUMENTS

| | | |
|---|---|---|
| 2,666,768 | 6/1952 | Ulich et al. ........................... 552/212 |
| 3,234,242 | 2/1966 | Basel et al. ........................... 552/212 |
| 3,471,524 | 10/1969 | Wick et al. ........................... 552/212 |
| 3,900,472 | 8/1975 | Chang .................................... 552/212 |
| 4,318,848 | 3/1982 | Han-Heinz et al. .................. 552/212 |

FOREIGN PATENT DOCUMENTS

| | | | |
|---|---|---|---|
| 251457 | 5/1963 | Australia ............................. 552/212 |
| 1546120 | 11/1968 | France ................................. 552/212 |
| 787716 | 12/1957 | United Kingdom ................ 552/212 |
| 926514 | 5/1963 | United Kingdom ................ 552/212 |
| 1149819 | 4/1969 | United Kingdom ................ 552/212 |

OTHER PUBLICATIONS

*Chemical Abstracts* 60:698e.

*Primary Examiner*—Marianne M. Cintins
*Assistant Examiner*—Keith MacMillan
*Attorney, Agent, or Firm*—Cushman Darby & Cushman

[57] ABSTRACT

Crude 4,4'-diamino-1,1'-dianthraquinonyl-3,3'-disulfonic acids or salts thereof are purified by subjecting an aqueous solution containing the crude products to salting-out using inorganic salts, the aqueous solution being adjusted within a range of from acid to neutral region, whereby a product usable as such for the production of 4,4'-diamino-1,1'-dianthraquinonyl red pigments having excellent pigmentary properties is obtained in high yields with industrial advantages.

12 Claims, No Drawings

PROCESS FOR PURIFICATION OF CRUDE 4,4'-DIAMINO-1,1'-DIANTHRAQUINONYL-3,3'-DISULFONIC ACIDS AND SALTS THEREOF

This is a continuation of application No. 0 7/818,146, filed on Jan. 8, 1992, now abandoned.

The present invention relates to a process for purification of crude 4,4'-diamino1,1'-dianthraquinonyl-3,3'-disulfonic acids or salts thereof.

4,4'-Diamino-1,1'-dianthraquinonyl-3,3'disulfonic acids (hereinafter referred to as disulfonic acids for brevity) and their salts such as alkali metal salts are useful as intermediates for the production of 4,4'-diamino-1,1'-dianthraquinonyl red pigments useful for various fields such as paints, printing inks and plastics, and produced by allowing 1-amino-4-halogenoanthraquinone-2-sulfonic acids to react with each other in the presence of metallic copper or copper compounds in an acidic medium under heating, as disclosed, for example, in JP-B-38-125842.

However, the thus produced disulfonic acids and their salts as such are hardly used for the production of the red pigments, because the pigments produced using them are dark bluish red in their tint and inferior in their pigmentary properties.

Therefore, purification of the crude disulfonic acids and salts thereof produced in a known manner becomes necessary.

For example, the afore-said JP-B-38-25842 discloses also purification processes which are, however, very complicated. One of them is as follows.

After the reaction is over, the reaction mixture is made alkaline, boiled and then subjected to hot-filtration. The obtained filtrate is mixed with sodium chloride under heating, and then cooled to precipitate crystals of the disulfonic acid in the form of sodium salt. The crystals collected on a filter are again dissolved in hot water. The solution is subjected to treatment with active carbon, and then the separated clear solution is subjected to salting-out using sodium chloride, thereby obtaining purified disulfonic acid in the form of sodium salt.

One object of the present invention is to provide a process for purification of the crude disulfonic acids or salts thereof, which are advantageous from industrial point of view.

Another object of the present invention is to provide a process for producing disulfonic acids or salts thereof which are usable as such for the production of 4,4'-diamino-1,1'-dianthraquinonyl red pigments, in high yields with industrial advantages.

These and other objects can be accomplished by providing a process for purification of a crude 4,4'-diamino-1,1'-dianthraquinonyl-3,3'-disulfonic acid or a salt thereof, which comprises mixing an inorganic salt with an aqueous solution containing the crude disulfonic acid or the salt thereof to effect salting-out, the aqueous solution being adjusted to from acid to neutral region after or before the mixing.

In carrying out the present invention, the crude disulfonic acids or salts thereof can be readily prepared by the reaction using 1-amino-4-halogenoanthraquinone-2-sulfonic acids or salts thereof such as 1-amino-4-bromoanthraquinone-2sulfonic acid or sodium salt thereof and metallic copper or copper compounds, in a known manner, for example, as disclosed in the afore-said JP-B-38-25842.

After the above-mentioned reaction is over, the reaction mixture is subjected to hot-filtration for removing copper compounds formed during the reaction, and the thus obtained filtrate can be used as the aqueous solution containing the crude disulfonic acids or salts thereof in the present invention.

The hot-filtration can be carried out without pH adjustment or after adjusting the pH within a range of from neutral to weak alkaline region using an alkali agent such as sodium hydroxide and sodium carbonate.

Although concentration of the disulfonic acids or salts thereof in the aqueous solution is not particularly limited, it is preferred to adjust the concentration within a range of preferably about 3 to 10% by weight, more preferably about 4 to 7% by weight in terms of sodium salts based on the weight of the aqueous solution.

The aqueous solution is adjusted to from acid to neutral region, preferably to a pH ranging from about 1 to 5, more preferably about 1 to 3, using the afore-said alkali agents or mineral acids such as sulfuric acid or hydrochloric acid. The pH adjustment of the aqueous solution may be carried out at any temperature.

The inorganic salts used for the salting-out include, for example, alkali metal salts such as sodium chloride, potassium chloride, sodium sulfate, potassium sulfate and the like, and alkaline earth metal salts such as calcium chloride and the like. The inorganic salts may be used each alone or in a mixture of two or more. Of these, alkali metal salts are preferred. Particularly preferred are sodium chloride, sodium sulfate or a mixture thereof.

The mixing of the inorganic salt with the aqueous solution can be carried out in a conventional manner such as addition of the inorganic salt to the aqueous solution under stirring. Alternatively, the inorganic salt may be formed in the aqueous solution using corresponding acids and bases.

The inorganic salts are used in an amount of preferably from about 1 to 5% by weight, more preferably from about 1 to 3% by weight, based on the weight of the aqueous solution. In the present invention, the mixing is preferably carried out by adding the inorganic salt to the aqueous solution at a temperature of preferably from 70° to 100° C., more preferably from 75° to 95° C.

After the mixing of the inorganic salt with the aqueous solution, the mixture is kept preferably under stirring at a temperature of preferably from 20° to 60° C., more preferably from 30° to 40° C. to effect the salting-out, in other words-to complete the crystallization of disulfonic acids or salts thereof.

Crystals of the disulfonic acids or salts thereof prepared in advance may be used as a seed crystal in an amount of from 1 to 5% by weight, preferably from 1 to 3% by weight, based on the weight of the disulfonic acids or salts thereof in the aqueous solution. The addition of the seed crystal may be carried out before or after the mixing of the inorganic salt with the aqueous solution.

In the present invention, although the adjustment of concentration of the disulfonic acids or salts thereof, adjustment of pH of the aqueous solution and mixing of the inorganic salt with the aqueous solution can be carried out in an optional order, it is preferred that the aqueous solution having a predetermined concentration of disulfonic acids or salts thereof is adjusted to a desired pH and then mixed with the inorganic salt.

More specifically, high purity disulfonic acids or salts thereof which can be used as such for the production of 4,4'-diamino1,1'-dianthraquinonyl red pigments, can be produced in the following preferable manner.

1-Amino-4-halogenoanthraquinone-2sulfonic acids or salts thereof, such as, for example, sodium 1-amino-4-bromoanthraquinone-2-sulfonate, are allowed to react in the presence of metallic copper or copper compounds in an acidic medium at a temperature of 50° to 100° C. in a conventional manner. After the reaction is over, the reaction mixture is made alkaline and then filtered at that temperature to remove the formed copper compounds. The filtrate having a desired concentration of alkali salts of disulfonic acids is adjusted to a desired pH using mineral acids such as sulfuric acid and hydrochloric acid. Thereafter, a predetermined amount of inorganic salts is added thereto at a temperature of 70° to 100° C. The mixture is stirred at a temperature of 20° to 60° C. to complete crystallization, and then filtered. Crystals collected on a filter may be washed with an aqueous solution containing the inorganic salts, and if desired, dried, thereby obtaining the desired product having high purity with high yields.

The product obtained in accordance with the present invention is in the form of a free acid or an alkali or alkaline earth metal salt, preferably, such as sodium or potassium salt.

According to the process of the present invention, the disulfonic acids or salts thereof purified so as to be used as such for the production of 4,4'-diamino-1,1'-dianthraquinonyl red pigments can be obtained in high yields in a more advantageous manner from industrial point of view, as compared with those of afore-said prior art, and using them the red pigments having excellent pigmentary properties can be obtained.

The present invention is illustrated in more detail with reference to the following Examples which are only illustrative, but not limitative. In Examples, parts and % are by weight.

EXAMPLE 1

Using sodium 1-amino-4-bromoanthraquinone2-sulfonate, copper powder, sulfuric acid and water, the reaction was carried out in accordance with Example 1 of JP-B-38-25842. After the reaction was over, the reaction mixture was made alkaline using sodium carbonate and then filtered to obtain an aqueous solution containing disodium 4,4'-diamino-1,1'-dianthraquinonyl-3,3'disulfonate as a filtrate. The aqueous solution (610 parts) containing disodium 4,4'-diamino-1,1'-dianthraquinonyl-3,3'-disulfonate (31.4 parts) was heated to 90° C. and adjusted to pH 3 using sulfuric acid. Then, sodium chloride (18.3 parts) was added thereto, and the mixture was allowed to cool to 40° C., while being stirred. Crystals precipitated were collected on a filter, washed with an aqueous sodium chloride solution and dried to obtain disodium 4,4'-diamino-1,1'-dianthraquinonyl-3,3'-disulfonate (30.6 parts) as dark red crystals.

The purity calculated by the following formula was found to be 99.4%.

Purity(%) = [disodium 4,4'-diamino-1,1'-dianthraquinonyl-3,3'-disulfonate content(%)]/100-[water(%) + total content of alkali metal salts(%)] × 100

EXAMPLE 2

A disodium 4,4'-diamino-1,1'-dianthraquinonyl-3,3'-disulfonate (31.4 parts)-containing aqueous solution (610 parts) obtained in the same manner as in Example 1 was heated to 90° C. and adjusted to pH 2 using sulfuric acid. Sodium sulfate (18.3 parts) was added thereto at that temperature, and the mixture was allowed to cool to 30° C., while being stirred. Crystals were collected on a filter, washed with an aqueous sodium sulfate solution and then dried to obtain disodium 4,4'-diamino-1,1'-dianthraquinonyl-3,3'-disulfonate as dark red crystals in high yield. The purity calculated was found to be 99.6%.

EXAMPLE 3

A disodium 4,4'-diamino-1,1'-dianthraquinonyl-3,3'-disulfonate-containing aqueous solution obtained in the same manner as in Example 1 was heated to 80° C., and adjusted to pH 1.5 using sulfuric acid. Sodium chloride (12.2 parts) and the disodium 4,4'-diamino-1,1'-dianthraquinonyl-3,3'-disulfonate crystals (0.3 part) obtained in Example 1 as a seed crystal were added thereto at that temperature, and the mixture was allowed to cool to 50° C., while being stirred. Crystals collected on a filter were washed with an aqueous sodium chloride solution, and then dried to obtain disodium 4,4'-diamino-1,1'-dianthraquinonyl3,3'-disulfonate as dark red crystals in high yield. The purity calculated was found to be 99.5%.

EXAMPLE 4

A disodium 4,4'-diamino-1,1'-dianthraquinonyl-3,3'-disulfonate-containing aqueous solution obtained in the same manner as in Example 1 was heated to 90° C., and adjusted to pH 4Sodium sulfate (9.1 parts) and sodium chloride (9.1 parts) were added thereto at that temperature, and the mixture was allowed to cool to 30° C., while being stirred. Crystals collected on a filter were washed with an aqueous solution containing sodium sulfate and sodium chloride, and then dried to obtain disodium 4,4'-diamino-1,1'-dianthraquinonyl3,3'-disulfonate as dark red crystals in high yield. The purity calculated was found to be 99.3%.

We claim:

1. A process for preparation of disulfonic acid intermediates of 4,4'-diamino-1,1'-dianthraquinonyl red pigments from a crude 4,4'-diamino-1,1'-dianthraquinonyl-3,3'-disulfonic acid or salt thereof, which comprises mixing an inorganic salt with an aqueous solution containing the crude disulphonic acid or the salt thereof to effect salting-out, the aqueous solution being adjusted to an acidic pH after or before the mixing.

2. The process according to claim 1, wherein the inorganic salt is used in an amount of about 1 to 5% by weight based on the weight of the aqueous solution.

3. The process according to claim 1, wherein the inorganic salt is selected from alkali metal salts and alkaline earth metal salts.

4. The process according to claim 1, wherein the inorganic salt is selected from sodium chloride, sodium sulfate and a mixture thereof.

5. The process according to claim 1, wherein concentration of the 4,4'-diamino-1,1'-dianthraquinonyl-3,3'-disulfonic acid or the salt thereof in the aqueous solution ranges from about 4 to 7% by weight based on the weight of the aqueous solution.

6. The process according to claim 1, wherein the mixing of the inorganic salt with the aqueous solution is carried out at a temperature of 70° to 100° C.

7. The process according to claim 1, wherein the aqueous solution is adjusted to a pH ranging from about 1 to 5 after or before the mixing.

8. The process according to claim 1, wherein the aqueous solution is adjusted to a pH ranging from about 1 to 5, and then the mixing of the inorganic salt with the aqueous solution is carried out.

9. The process according to claim 1, wherein the mixing of the inorganic salt with the aqueous solution is carried out at a temperature of 70° to 100° C., and then the mixture is kept at a temperature of 20° to 60° C. to effect the salting-out.

10. The process according to claim 1, wherein the aqueous solution is prepared by allowing a 1-amino-4-halogenoanthraquinone-2-sulfonic acid or a salt thereof to react in the presence of metallic copper or a copper compound in an acidic medium under heating, making the reaction mixture alkaline and then subjecting the resulting reaction mixture to hot-filtration, whereby the aqueous solution is obtained as a filtrate.

11. A process for producing a 4,4'-diamino1,1'-dianthraquinonyl-3,3'-disulfonic acid or a salt thereof, which comprises preparing an aqueous solution containing a crude 4,4'-diamino-1,1'-dianthraquinonyl-3,3'-disulfonic acid or a salt thereof, and mixing an inorganic salt with the aqueous solution to effect salting-out, the aqueous solution being adjusted to an acidic PH after or before the mixing of the inorganic salt with the aqueous solution, whereby a 4,4'-diamino-1,1'-dianthraquinonyl-3,3'-disulfonic acid or a salt thereof useful as such for production of a 4,4'-diamino-1,1'-dianthraquinonyl red pigment is produced.

12. The process according to claim 11, wherein the aqueous solution containing a crude 4,4'-diamino-1,1'-dianthraquinonyl-3,3'-disulfonic acid or a salt thereof is prepared by allowing a 1-amino-4-halogenoanthraquinone-2-sulfonic acid or a salt thereof to react in the presence of metallic copper or a copper compound in an acidic medium under heating, making the reaction mixture alkaline, and subjecting the resulting reaction mixture to hot-filtration to remove a copper compound formed during the reaction.

* * * * *